US00PP32779P2

(12) United States Plant Patent
Olesen

(10) Patent No.: US PP32,779 P2
(45) Date of Patent: Feb. 2, 2021

(54) MINIATURE ROSE PLANT NAMED 'POULPAR112'

(50) Latin Name: ***Rosa* hybrid**
Varietal Denomination: Poulpar112

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,258

(22) Filed: Sep. 4, 2019

(51) Int. Cl.
*A01H 5/02* (2018.01)
*A01H 6/74* (2018.01)

(52) U.S. Cl.
USPC ..... Plt./118

(58) Field of Classification Search
USPC ..... Plt./101, 116, 118
See application file for complete search history.

(56) References Cited

PUBLICATIONS

Poulsen Roser website. 2020. (http://www.poulsenroser.com/assortment/rose-collections/parade/tereza.aspx). 2 pages. (Year: 2020).*

* cited by examiner

*Primary Examiner* — Susan McCormick Ewoldt
*Assistant Examiner* — Karen M Redden

(57) ABSTRACT

A new garden rose plant of the miniature class which has abundant, yellow flowers and attractive foliage. This new and distinct variety has shown to be uniform and stable in the resulting generations from asexual propagation.

1 Drawing Sheet

Botanical designation: *Rosa* hybrid.
Variety denomination: 'Poulpar112'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpar112', originated as a single seedling from the stated cross.

The new variety may be distinguished from its male pollen parent and female seed parent primarily by the following characteristics. The male pollen parent plant has ivory white flowers while the new variety has yellow flowers. The female seed parent plant has light yellow flowers while the new variety has yellow flowers.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpar112' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpar112' was selected in the spring of 2011 by the inventor as a single plant from the progeny of the aforementioned hybridization.

Asexual reproduction of 'Poulpar112' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpar112' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar112'. Specifically illustrated in the drawing are open flowers, flower bud, flower petals detached, sepals detached revealing reproductive flower parts, juvenile leaves, mature leaf, and bare stem. Plants shown are 2 years of age.

DETAILED DESCRIPTION OF THE VARIETY

The following is a description of 'Poulpar112', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar083', U.S. Plant Pat. No. 26,898 are compared to 'Poulpar112' in Chart 1.

CHART 1

| | 'Poulpar112' | 'Poulpar083' |
|---|---|---|
| Petal Count | 35 | 30 petals |
| Flower Diameter | 60 mm | 60 mm |
| General Tonality of Flower Color | Yellow Group 12A | Yellow Group 13B |

FLOWER AND FLOWER BUD

Blooming habit: Continuous.

Flower bud:

*Size.*—Upon opening, 25 mm in length from base of receptacle to end of bud. Bud diameter is 14 mm.

*Bud form.*—Ovoid.

*Bud color.*—As sepals divide petals are Yellow Group 8A with other intonations of Orange-Red Group N34B.

*Sepal inner surface.*—Color: Yellow-Green Group 145B. Surface: Lightly pubescent.

*Sepal outer surface.*—Color: Yellow-Green Group 144A with intonations of Greyed-Orange Group 171A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—25 mm long, 10 mm wide.

*Receptacle.*—Texture: Smooth. Size: 6 mm in height, 9 mm wide. Color: Yellow-Green Group 144A. Shape: Funnel shaped.

*Pedicel.*—Surface: Smooth. Length: 25 mm. Diameter: 3 mm on average. Color: Yellow-Green Group 144A. Strength: Strong.

*Peduncle.*—Length: 1 to 3 cm. Diameter: About mm. Color: Yellow-Green Group 145A. Texture: Smooth.

Flower bud development: Flower buds are borne singly or in clusters of up to 5 flower buds per stem.

Flower bloom:

*Fragrance.*—Mild floral scent.

*Duration.*—The blooms have a duration on the plant of approximately 10 days. Petals fall cleanly away from plant after flowers have fully matured.

*Size.*—Flower diameter is 60 mm when open. Flower depth is 23 mm.

*Flower shape.*—Rosette, with many overlapping petals of different sizes.

*Shape of flower, side view.*—The upper portion is flat convex. The lower portion is a flattened concave.

*Petalage.*—Under normal conditions, flowers have about 35 petals.

General tonality of flower: Open flowers are Yellow Group 12A.

Petal color:

*Upon opening, outer and inner petals.*—Upper surface: Yellow Group 12A. Lower surface: Yellow Group 11A.

*After opening, outer petals.*—Upper surface: Yellow Group 10A. Lower surface: Yellow Group 8A.

*Basal petal spots.*—No distinctive coloration at the petal base observed.

Petals:

*Petal reflex.*—Strong.

*Margin.*—Entire and uniform. Moderate undulations.

*Shape.*—Broad and elliptic. Apex shape: Rounded. Base shape: Acute.

*Size.*—30 mm (l)×36 mm (w).

*Texture.*—Smooth.

*Thickness.*—Average.

Petaloids:

*Size.*—9 mm (l) by 4 mm (w).

*Quantity.*—About 4.

*Shape.*—Elliptical with an acute base and rounded apices.

*Color.*—The upper surface Yellow Group 12A. The undersurface is Yellow Group 11A.

Reproductive flower parts:

*Pollen.*—None observed.

*Anthers.*—Size: 2 mm in length. Color: Greyed-Orange Group N167A. Quantity: 65 on average.

*Filaments.*—Color: Yellow-Orange Group 14B. Length: 4 mm.

*Pistils.*—Length: 5 mm. Quantity: 35 on average.

*Stigmas.*—Color: Greyed-Yellow Group 162C.

*Styles.*—Color: Green-White Group 157A.

*Location of stigmas.*—Inferior in location relative to the length of the filaments and the height of the anthers.

*Hips.*—None Observed.

PLANT

Plant growth: Upright, bushy. Plants are about 20 cm in height, and 20 cm wide.

Stems:

*Color of juvenile growth.*—Yellow-Green Group 144A.

*Color of mature growth.*—Yellow-Green Group 144A.

*Length.*—Canes are about 12 cm from the base of the plant to the flowering portion.

*Diameter.*—About 5 mm.

*Internodes.*—On mature canes about 13 mm between nodes.

*Surface texture.*—Young wood: Smooth. Older wood: Smooth.

Long prickles: None observed.

Plant foliage:

*Compound leaf.*—85 mm (l)×60 (w).

*Quantity.*—About 7 leaves per 10 cm of stem on average.

*Leaf bearing angle to the stem.*—45 degrees.

*Color of juvenile foliage.*—Upper side: Yellow-Green Group 144A with marginal intonations of Greyed-Red Group 181A. Lower side: Yellow-Green Group 144A with marginal intonations of Greyed-Red Group 181A.

*Color of mature foliage.*—Upper side: Yellow-Green Group 146A. Lower side: Yellow-Green Group 146B.

Plant leaves and leaflets:

*Stipules.*—Size: 5 mm long, mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 1.5 mm. Upper surface color: Yellow-Green Group 144A. Lower surface color: Yellow-Green Group 144A.

*Rachis*.—Length: 23 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 25 mm long, 20 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpar112', substantially as illustrated and described herein, due to its abundant yellow flowers, disease resistance, and extended period of bloom.

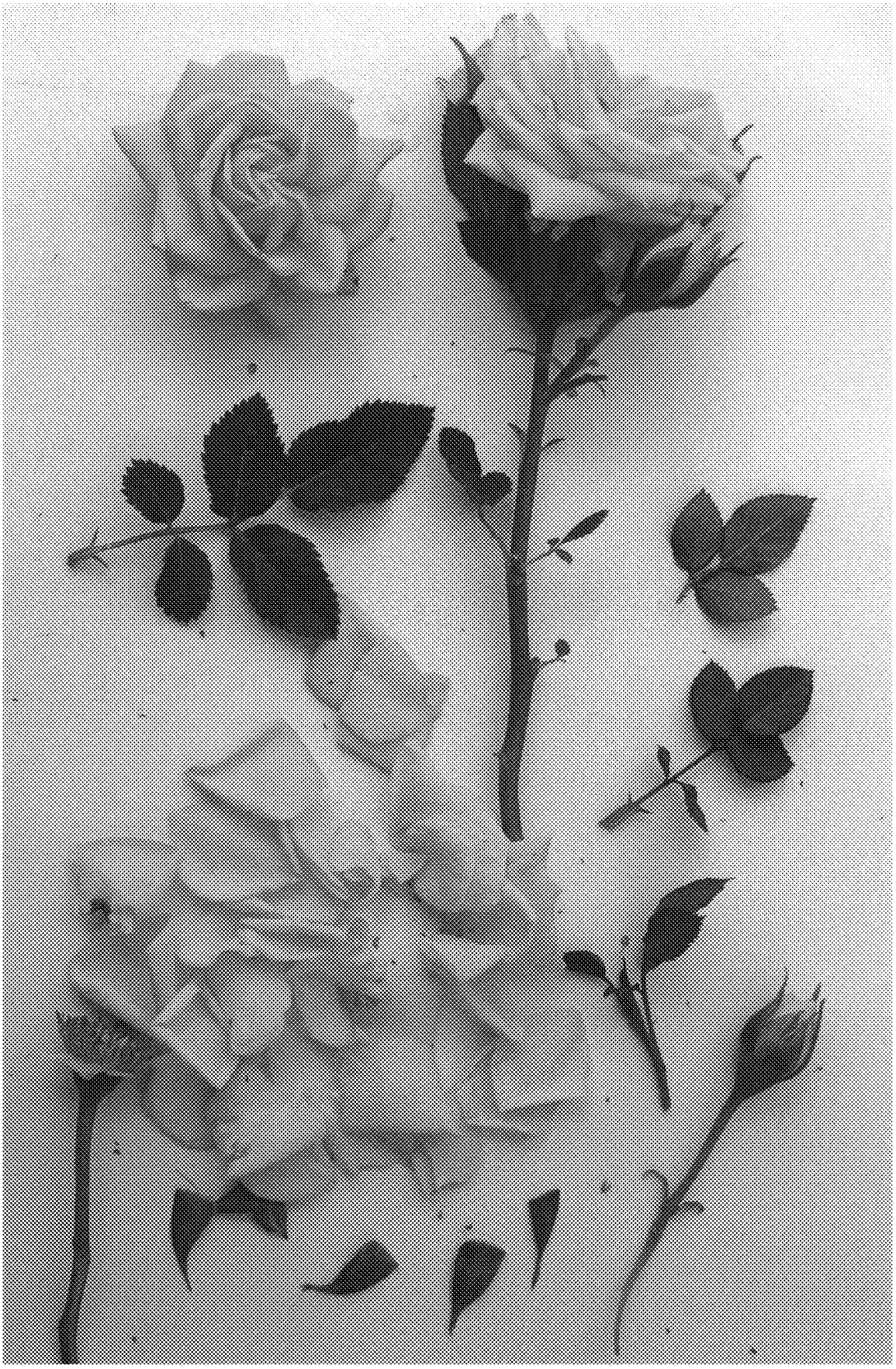

* * * * *